(12) United States Patent
Randall

(10) Patent No.: US 6,803,469 B2
(45) Date of Patent: Oct. 12, 2004

(54) PROCESS FOR PREPARING QUINOLONE ANTIBIOTIC INTERMEDIATES

(75) Inventor: Jared Lynn Randall, Smyrna, NY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/630,608

(22) Filed: Jul. 30, 2003

(65) Prior Publication Data

US 2004/0063952 A1 Apr. 1, 2004

Related U.S. Application Data

(60) Provisional application No. 60/401,184, filed on Aug. 5, 2002.

(51) Int. Cl.[7] ............................................. C07D 215/56
(52) U.S. Cl. ........................................................ 546/196
(58) Field of Search ........................................... 546/196

(56) References Cited

U.S. PATENT DOCUMENTS 4,695,646 A * 9/1987 Maurer et al. ................. 560/43
5,703,231 A 12/1997 Randall et al.

FOREIGN PATENT DOCUMENTS

| WO | WO 96/04247 | 2/1996 |
| WO | WO 96/04286 | 2/1996 |
| WO | WO 02/48113 | 6/2002 |

* cited by examiner

Primary Examiner—Bernard Dentz
(74) Attorney, Agent, or Firm—Richard S. Echler, Sr.

(57) ABSTRACT

The present invention relates to a process for preparing a quinolone antibiotic intermediate having the formula:

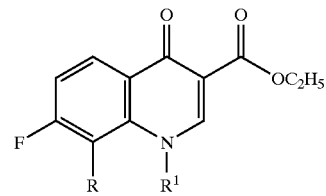

wherein R is $C_1$–$C_2$ alkyl, $C_1$–$C_2$ fluoroalkyl, $C_2$–$C_4$ alkenyl, methoxy, chloro, or bromo; $R^1$ is a unit selected from the group consisting of $C_1$–$C_2$ alkyl, $C_2$–$C_3$ alkenyl, $C_3$–$C_5$ cycloalkyl, and phenyl, each of which can be substituted by one or more fluorine atoms; said process comprising the step of cyclizing an admixture of quinolone precursors, said admixture comprising a 2-ethoxy substituted intermediate having the formula:

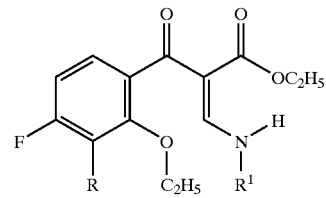

in the presence of a silylating agent.

25 Claims, No Drawings

PROCESS FOR PREPARING QUINOLONE ANTIBIOTIC INTERMEDIATES

CROSS REFERENCE TO RELATED APPLICATION

This application claims priority under Title 35, United States Code 119(e) from Provisional Application Ser. No. 60/401,184, filed Aug. 5, 2002.

FIELD OF THE INVENTION

The present invention relates to a process for preparing quinolone antibiotic intermediates. The process of the present invention utilizes the surprising result that 3-(2-alkoxyphenyl)-2-enamine-3-oxo-propionic acid ester by-products can be carried forward and are suitable intermediates for the final quinolone products.

BACKGROUND OF THE INVENTION

Quinolone and quinolonyl antibiotics are a recent class of highly potent, broad spectrum antimicrobials and research has been directed at developing this new class of antimicrobials, especially those effective against Gram positive pathogens, inter alia, vancomycin-resistant *Enterococcus faecium*. These quinolone and quinolonyl antibiotics and their preparation are well described in the documents cited herein below.

However, some categories of quinolone antibiotic analogs have substituents along the quinolone ring system which render the synthesis of these analogs cumbersome, indirect, and only achievable in low overall yield. There is therefore a long felt need for a process for making the quinolone and quinolonyl antibiotic intermediates described herein, said process encompassing a direct, high yield, low cost series of reactions thereby benefiting the consumer with effective, affordable antibiotics.

SUMMARY OF THE INVENTION

The present invention relates to the surprising discovery that quinolone antibiotic intermediates having the formula:

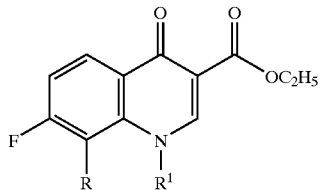

wherein R is $C_1$–$C_2$ alkyl, $C_1$–$C_2$ fluoroalkyl, $C_2$–$C_4$ alkenyl, methoxy, chloro, or bromo; $R^1$ is a unit selected from the group consisting of $C_1$–$C_2$ alkyl, $C_2$–$C_3$ alkenyl, $C_3$–$C_5$ cycloalkyl, and phenyl, each of which can be substituted by one or more fluorine atoms; can be prepared by reacting an admixture of quinolone antibiotic intermediate precursors, said admixture comprising a 2-ethoxy substituted intermediate having the formula:

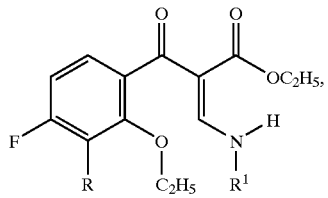

with a silylating agent as a ring closure reaction catalyst.

In general the present invention relates to a process for preparing quinolone antibiotic intermediates having the formula:

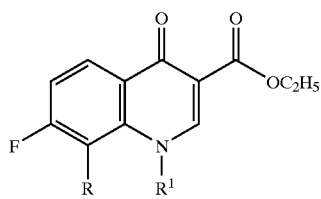

wherein R and $R^1$ are defined herein; said process comprising the steps of:

a) reacting an acetophenone having the formula:

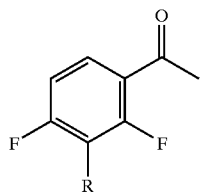

with diethylcarbonate in the presence of a base to form an admixture of 4-fluoro β-ketoesters having the formula:

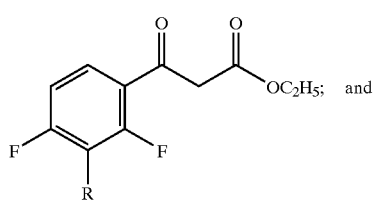

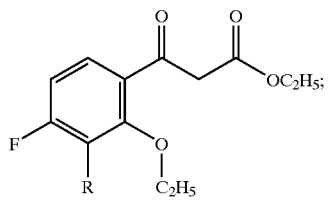

b) reacting said admixture with an amine capable of undergoing a Knoevenagel Reaction, said amine having the formula:

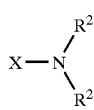

wherein $R^2$ is $C_1$–$C_4$ linear or branched alkyl, phenyl, and mixtures thereof; X is an aldehyde unit or an aldehyde unit equivalent; to form an admixture of enamine intermediates having the formula:

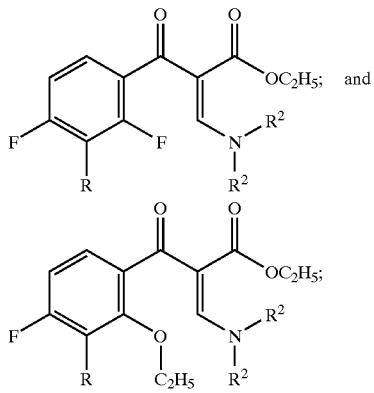

c) reacting said enamine intermediate admixture with an amine having the formula:

$R^1$—$NH_2$ to form an admixture of quinolone intermediates having the formula:

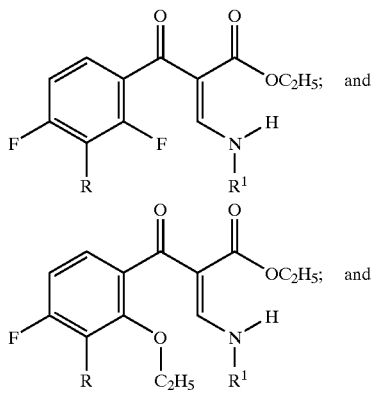

d) cyclizing said quinoline intermediate admixture in the presence of a silylating agent to form the quinoline antibiotic intermediates according to the present invention.

The present invention further relates to novel compounds having the formula:

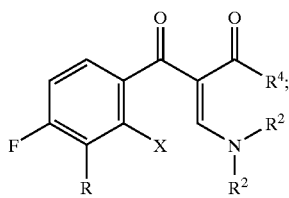

and the formula:

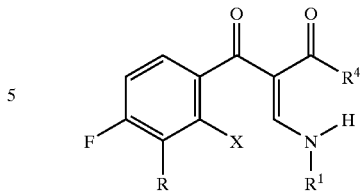

wherein R, $R^1$, and $R^4$ are defined herein above, X is a suitable leaving group, said compounds suitable for use as intermediates in the preparation of quinolone antibiotics according to the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The present invention relates to the surprising discovery that 1-lower alkyl-8-substituted quinolones, inter alia, 1-cyclopropyl and 1-ethyl-8-methoxyquinolone carboxylic acids of the formula:

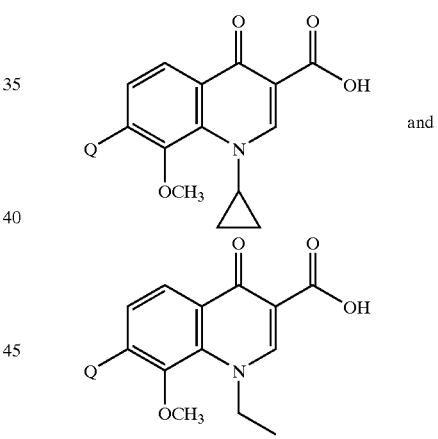

wherein Q is an amino-substituted pyrrolidine or piperidine, inter alia, units having the formula:

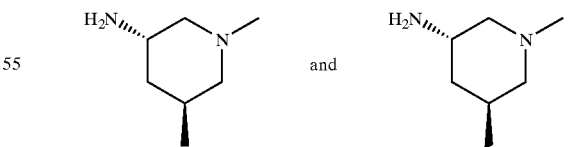

display high levels of efficacy toward Gram positive bacteria.

As a result of this surprising discovery, there developed a long felt need for a high yield, low cost convergent synthesis for antibiotics of this compound class. In addition, there developed a desire for a process adaptable to the broadest range of analogs comprising this class of antibiotics.

Our investigation of quinolone antibiotics of this category is well disclosed in U.S. Pat. No. 6,329,391 B1 Ledoussal et al., issued Dec. 11, 2001 and U.S. Pat. No. 6,387,928 B1 Ledoussal et al., issued May 14, 2002, both of which are incorporated herein by reference. The process described therein involved reaction conditions and procedures which protected against the unwanted elimination of the 2-position fluorine atom during the preparation of quinolone antibiotic precursors, one of which has the formula:

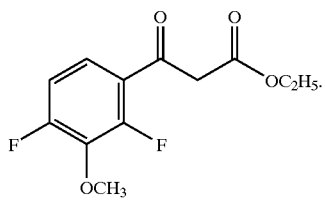

In our endeavor to provide a low cost, high yield process for preparing quinolone antibiotics, we desired to affect ring closure of 2-enamino-β-ketoester quinolone antibiotic precursor intermediates having the general formula:

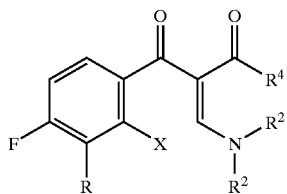

wherein X is a leaving group and $R^4$ is a moiety which is compatible with the ring closure reaction conditions. To achieve these quinolone antibiotic intermediates we began our process by reacting 3-substituted-2,4-difluorobenzophenones with diethylcarbonate in the expectation of forming the corresponding β-ketoester. However, analysis of the products which result from the reaction of diethylcarbonate with 2,4-difluoro-3-methoxybenzophenone indicated an admixture of products as outlined below

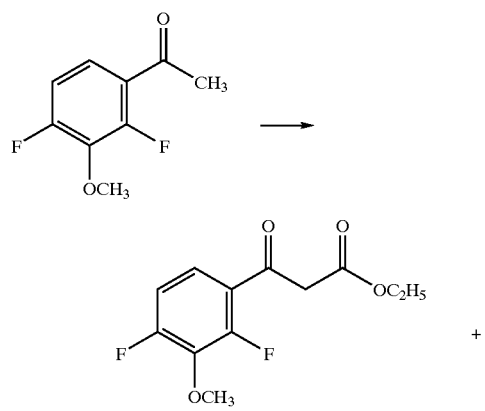

-continued

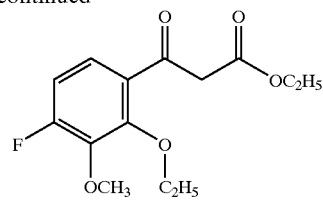

wherein a substantial amount of the 2-position fluorine atom had been displaced by an ethoxy unit in an unwanted side reaction.

It has now been surprisingly discovered that the presence of an impurity having the general formula:

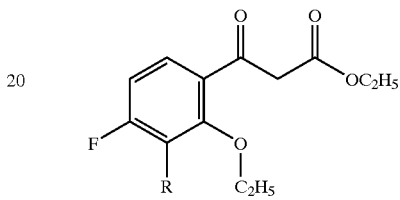

which is formed in substantial amounts as a by product of the reaction of 3-substituted 2,4-difluorobenzophenones with diethylcarbonate, can be successfully cyclized, together with the corresponding 2-fluoro adduct, in a ring closure reaction which affords the desired quinolone antibiotic intermediate in high yield and under mild conditions. It has also been surprisingly discovered that the R unit can be extended to include $C_1$–$C_2$ alkyl, $C_1$–$C_2$ fluoroalkyl, $C_2$–$C_4$ alkenyl, chloro, or bromo, as well as methoxy.

Process Intermediates

The process of the present invention described herein below, utilizes novel compounds as intermediates. These intermediates fall into two categories. The first category relates to β-ketoester enamines which are formed from the reaction of a secondary amine and a 3-aryl-3-oxo-propionic acid ester having the formula:

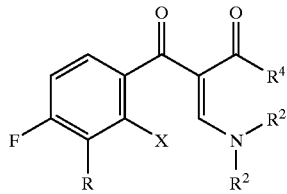

wherein R is $C_1$–$C_2$ alkyl, $C_1$–$C_2$ fluoroalkyl, $C_2$–$C_4$ alkenyl, methoxy, chloro, or bromo; $R^2$ is $C_1$–$C_4$ linear or branched alkyl, phenyl, and mixtures thereof; and $R^4$ is a unit which is compatible with the subsequent ring closure reaction conditions. Non-limiting examples of a unit which is suitable as $R^4$ is an alkoxy unit which results in the formation of a methyl ester. Ester are the most convenient moiety since the antibiotic which are formed form the intermediates described herein comprise a 3-carboxyquinolone.

A first aspect of the present invention as it relates to novel compounds encompasses R units equal to methoxy. An embodiment of this aspect of R has the formula:

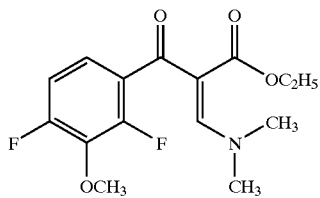

while another embodiment has the formula:

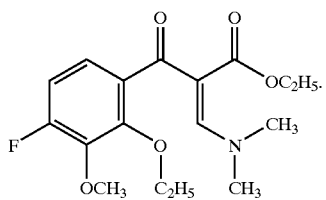

A second aspect relates to R units which are lower alkyl or fluorine substituted lower alkyl, iterations of which include —CH$_3$, —CH$_2$F, —CHF$_2$, and —CF$_3$.

A third aspect relates to R units comprising chloro or bromo. An embodiment of this aspect of R has the formula:

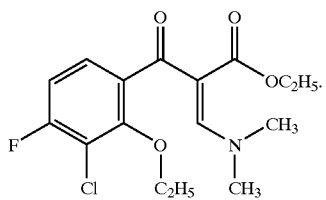

A fourth aspect relates to R units comprising an olefin, inter alia, —CH$_2$CH=CH$_2$.

The second category relates to β-ketoester enamines which are formed from the reaction of a secondary amine and a 3-aryl-3-oxo-propionic acid ester having the formula:

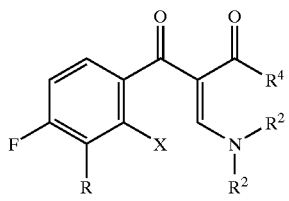

wherein R is C$_1$–C$_2$ alkyl, C$_1$–C$_2$ fluoroalkyl, C$_2$–C$_4$ alkenyl, methoxy, chloro, or bromo; R$^2$ is C$_1$–C$_4$ linear or branched alkyl, phenyl, and mixtures thereof; and R$^4$ is a unit which is compatible with the subsequent ring closure reaction conditions.

A first aspect relates to R equal to methoxy. An embodiment of this aspect of R has the formula:

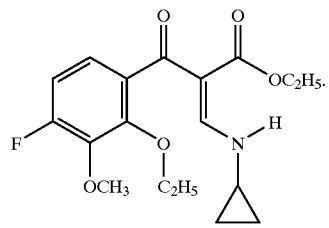

A second aspect relates to R units which are lower alkyl or fluorine substituted lower alkyl, iterations of which include —CH$_3$, —CH$_2$F, —CHF$_2$, and —CF$_3$.

A third aspect relates to R units comprising chloro or bromo. An embodiment of this aspect of R has the formula:

(structure)

A fourth aspect relates to R units comprising an olefin, inter alia, —CH$_2$CH=CH$_2$.

Process

The process of the present invention relates to the preparation of quinolone antibiotic intermediates having the formula:

(structure)

wherein R is C$_1$–C$_2$ alkyl, C$_1$–C$_2$ fluoroalkyl, C$_2$–C$_4$ alkenyl, methoxy, chloro, or bromo; R$^1$ is a unit selected from the group consisting of C$_1$–C$_2$ alkyl, C$_2$–C$_3$ alkenyl, C$_3$–C$_5$ cycloalkyl, and phenyl, each of which can be substituted by one or more fluorine atoms.

Step (a)

Step (a) of the present process relates to the reaction of a 3-substituted-2,4-difluorobenzophenone having the formula:

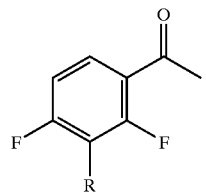

with diethylcarbonate in the presence of a base to form an admixture of 3-[2,4-difluoro-3-R-substituted]-3-oxo-propionic acid methyl ester:

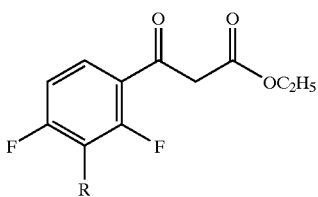

and 3-[2-ethoxy-3-R-substituted-4-fluoro]-3-oxo-propionic acid methyl ester:

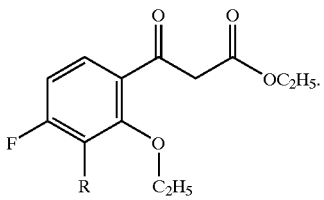

The stoichiometry of Step (a) requires at least one equivalent of diethylcarbonate per equivalent of benzophenone. However, other aspects of Step (a) utilize amounts of diethylcarbonate in excess of one mole equivalent.

The stoichiometry of Step (a) also requires at least one equivalent of base. Suitable bases include metal hydrides, for example, LiH, NaH, KH, $CaH_2$, an the like. One aspect relating to the selection of a base utilizes mineral oil suspension of NaH which can be used conveniently and safely in large scale, as well as small scale operations. Other bases include inorganic bases, inter alia, $Na_2CO_3$, $NaHCO_3$, and $K_2CO_3$ or organic bases, inter alia, butyl lithium and lithium diisopropylamide.

One aspect of the present invention relates to the use of an excess of diethylcarbonate. A first iteration of Step (a) wherein an excess of diethylcarbonate is used encompasses the concomitant use of excess base as well. A non-limiting example of Step (a) related to this aspect includes the reaction of one mole of a 2,4-difluoro-3-R-substituted benzophenone, 2.2 moles of a base, and 2.4 moles of diethylcarbonate.

The formulator may use an aprotic solvent for step (a) both to solublize the reagents and to provide an efficient heat transfer medium. Non-limiting examples of solvents include methylene chloride, dichloromethane, hexamethylphosphoramide, tetrahydrofuran, benzene, toluene, alkanes, inter alia, hexane, or mixtures of solvents. Most conditions require the use of moisture free solvents, however, the formulator may employ excess base to consume any residual or nascent water which is present. One aspect of the present invention relates to the use of toluene as a solvent, which in the case of processes which do not isolate intermediates, can be used to azeotropically dry the reaction product.

The temperature at which Step (a) is conducted is predicated on several factors, including the reactivity of the starting benzophenone, the choice of base, and the freezing/boiling point of any solvent which is used. One example of the present invention, as it relates to the temperature of step (a), is described herein below in Example 1 wherein the diethylcarbonate is slowly added to a suspension of the base (NaH) in toluene at 90° C. followed by addition of the acetophenone at 90° C.–95° C. However, depending upon the choice of reagents and the scale of the reaction, the formulator may choose to complete the reaction at lower temperatures.

One aspect relates to initial de-protonation of the benzophenone with an alkyl lithium reagent in the cold and allowing the solution to warm prior to addition of the diethylcarbonate.

Step (b)

Step (b) of the present invention relates to the reaction of the admixture formed in Step (a) with an adduct which is capable of undergoing a Knoevenagel or Knoevenagel-like reaction to form an admixture of N.N-disubstituted enamines having the formula:

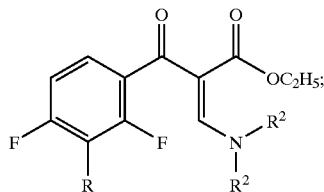

and the formula:

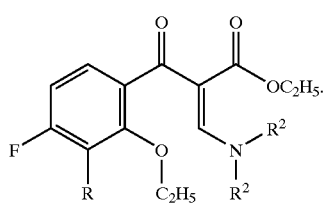

The adduct which is reacted with the β-ketoester admixture formed in Step (a) has the formula:

wherein $R^2$ is $C_1$–$C_4$ linear or branched alkyl, phenyl, and mixtures thereof; X is an aldehyde unit or an aldehyde unit equivalent. What is meant herein by the definition of X is that the adduct may be an aldehyde having the formula:

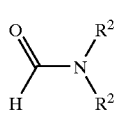

or an aldehyde equivalent, for example, a dimethyl acetal having the formula:

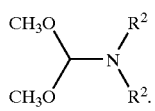

Depending upon the conditions of Step (b) the formulator may select any form for the adduct provided it is capable of forming the required admixture of enamines.

The stoichiometry of Step (b) requires at least one equivalent of the aldehyde or aldehyde-equivalent adduct per equivalent of benzophenone in all forms. However, other aspects of Step (b) utilize amounts of the adduct in excess of one mole equivalent.

One aspect of the present invention relates to the use of an excess of an adduct which comprises an aldehyde equivalent. A non-limiting example of Step (b) related to this aspect includes the reaction of one mole of the β-ketoester admixture with 1.5 mole equivalents of a dimethyl acetal having the formula:

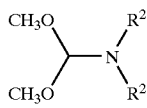

for example, the reaction as outlined herein below in Example 1.

Typically the β-ketoester admixture and the adduct are combined together at room temperature and heated. In the case of acetal comprising aldehyde equivalents, the reaction can be driven to completion by distilling off the alcohol which is released then the aldehyde carbonyl reacts with the β-ketoester admixture.

The formulator may use any solvent for Step (b), which does not react with the reagents under the conditions of the step, both to solublize the reagents and to provide an efficient heat transfer medium. Non-limiting examples of solvents include methylene chloride, dichloromethane, hexamethylphosphoramide, tetrahydrofuran, benzene, toluene, alkanes, inter alia, hexane, or mixtures of solvents. However, alcoholic solvents, especially in the presence of aldehyde equivalents may severely limit the reactivity of the adduct and therefore should not be used. One aspect of the present invention relates to the use of toluene as a solvent, which in the case of processes which do not isolate intermediates, can be used to azeotropically dry the reaction product.

The temperature at which Step (b) is conducted is predicated on several factors, including the reactivity of the aldehyde-comprising or aldehyde equivalent-comprising adduct and the freezing/boiling point of any solvent which is used. Example 1 herein below provides a suitable example for the temperature range at which each facet of Step (b) is conducted.

Step (c)

Step (c) of the present process relates to the reaction of the N.N-disubstituted enamine admixture formed in Step (b) with a primary amine having the formula:

$R^1-NH_2$ to form an admixture of quinolone intermediates having the formula:

and the formula:

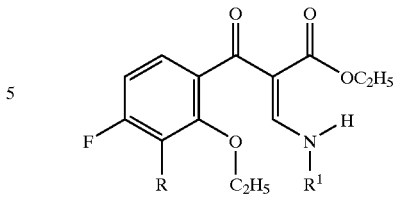

wherein $R^1$ is a unit selected from the group consisting of $C_1-C_2$ alkyl, $C_2-C_3$ alkenyl, $C_3-C_5$ cycloalkyl, and phenyl, each of which can be substituted by one or more fluorine atoms.

The stoichiometry of Step (c) requires at least one equivalent of the amine per total amount of enamine present in the admixture. However, other aspects of Step (c) utilize amounts of the amine in excess of one mole equivalent.

The formulator may use an aprotic solvent for step (c) both to solublize the reagents and to provide an efficient heat transfer medium. Non-limiting examples of solvents include methylene chloride, dichloromethane, hexamethylphosphoramide, tetrahydrofuran, benzene, toluene, alkanes, inter alia, hexane, or mixtures of solvents. Most conditions require the use of moisture free solvents, however, the formulator may employ excess base to consume any residual or nascent water which is present. One aspect of the present invention relates to the use of toluene as a solvent, which in the case of processes which do not isolate intermediates, can be used to azeotropically dry the reaction product.

Typically the amine can be added as a solution in a suitable solvent, or directly to the reaction admixture if the amine is a liquid. Step (c) may be conducted at any temperature which is sufficient to complete the reaction. One embodiment, which is exemplified in Example 1 herein below, conducts the reaction at room temperature.

One aspect of the present invention relates to the use of an excess of the amine. A first iteration of Step (c) wherein an excess of an amine is used encompasses a work-up for neutral product which comprises treatment of the reaction solution with acid.

The flexibility of the present process is manifest in the fact the formulator can optionally combine Steps (b) and (c) in manner wherein the admixture formed in Step (b) is not isolated, but instead is carried forward to Step (c). This option allows the formulator the advantage of large batch production of the quinolone antibiotic intermediates once the reaction parameters have been determined.

Step (d)

Step (d) of the present process relate to cyclizing the quinoline intermediate admixture formed in Step (c) in the presence of a silylating agent to form a quinoline antibiotic intermediate having the formula:

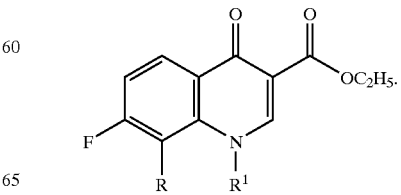

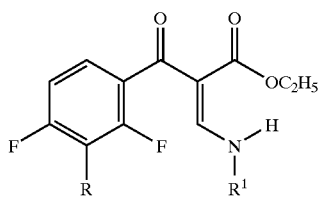

What is meant herein by "silylating agent" is any "organosilicon" compound or any-silicon-containing compound that is commonly utilized in silylation reactions, wherein a hydrogen atom, inter alia, nitrogen, oxygen, is substituted with a silyl group. Non-limiting examples of silyl groups include trimethylsilyl and phenyldimethylsilyl. Non-limiting examples of silylating agents include: chlorotrimethylsilane, N,O-bis(trimethyl-silyl)acetamide, N,O-bis(trimethylsilyl)trifluoroacetamide, bis (trimethylsilyl)urea, hexamethyltrisilazane, N-methyl-N-trimethylsilyltrifluoroacetamide, 1-trimethylsilyl-imidazole, trimethylsilyl trifluourmethanesulfonate, tert-butyldimethylchlorosilane, 1-(tert-butyldimethylsilyl) imidazole, N-tert-butyldimethyl-N-methyltrifluoroacetamide, tert-butyldimethylsilyltrifluoromethanesulfonate, tert-butylphenylchorosilane, tert-butyl-methoxyphenylbromosilane, dimethylphenylchlorosilane, triethylchlorosilane, trimethyl-silyl trifluoromethanesulfonate, and triphenylchlorosilane. The use of silylating agent is described by Cooper, B., "Silylation in Organic Synthesis", *Proc. Biochem.* 9, (1980) included herein by reference. The use of silylating agents for quinolone formation is further described in U.S. Pat. No. 5,801,242 Randall et al., issued Sep. 1, 1998; and U.S. Pat. No. 5,703,231 Randall et al., issued Dec. 30, 1997 both of which are incorporated herein by reference.

Not wishing to be limited by theory, the proposed stoichiometry of Step (d) requires at least one equivalent of silylating agent for each equivalent of enamine in the admixture formed in Step (c). However, other aspects of Step (d) utilize amounts of the silylating agent in excess of one mole equivalent.

The formulator may use an aprotic solvent for step (c) both to solublize the reagents and to provide an efficient heat transfer medium. Non-limiting examples of solvents include methylene chloride, dichloromethane, hexamethylphosphoramide, tetrahydrofuran, benzene, toluene, alkanes, inter alia, hexane, or mixtures of solvents, inter alia, hexane, or mixtures of solvents. Most conditions require the use of moisture free solvents, however, the formulator may employ excess base to consume any residual or nascent water which is present. One aspect of the present invention relates to the use of toluene as a solvent, which in the case of processes which do not isolate intermediates, can be used to azeotropically dry the reaction product.

Typically the silylating agents are liquids which can be added directly to the reaction solution of the enamine admixture formed in Step (c) or the silylating agents are low melting solids that can be added as a solution in a suitable solvent. Step (d) may be conducted at any temperature which is sufficient to complete the reaction. One embodiment, which is exemplified in Example 1 herein below, adds the silylating agent at room temperature then heats the reaction to reflux in a suitable solvent until the reaction is complete.

The flexibility of the present process allows for a continuous batch process wherein the intermediate admixtures do not have to be isolated from the product matrix and purified. It is also convenient that the steps of the present process can be conveniently monitored for completion by thin layer chromatography (TLC) or any conventional analytical HPLC system.

The first category of quinolone antibiotic intermediates which are capable of being prepared by the process of the present invention are 3-carboxyquinolone methyl esters having the formula:

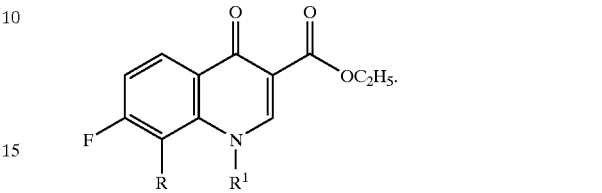

The following scheme and Example 1 illustrate the present process for preparing compounds of category one, wherein for the present example R is methoxy and $R^1$ is cyclopropyl.

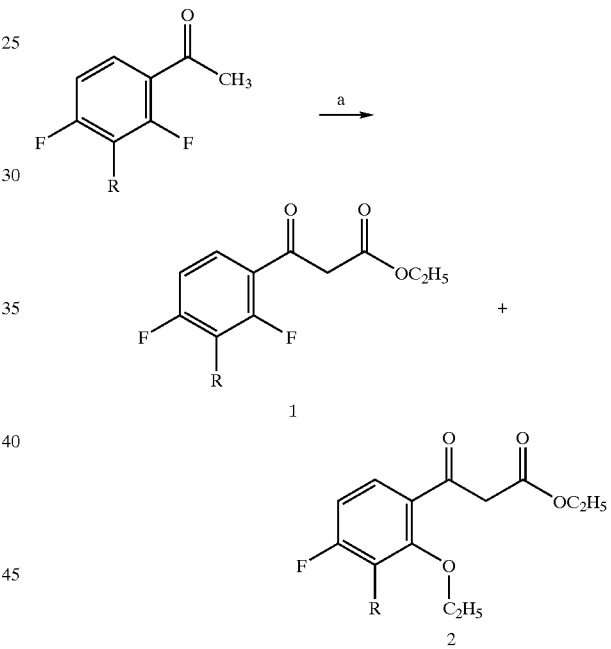

Reagents and conditions: (a) (EtO)$_2$CO, NaH, toluene, 90° C.–95° C., 1.5 hr.

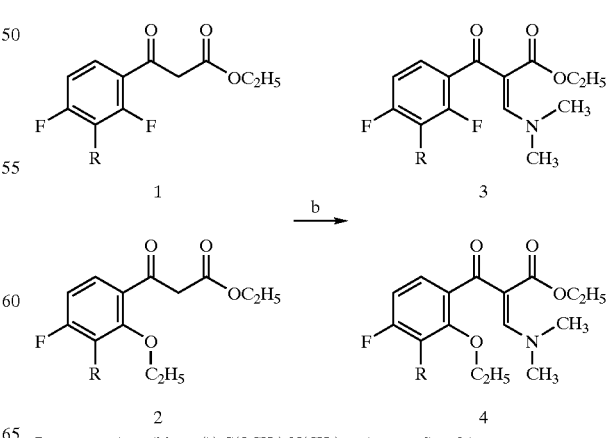

Reagents and conditions: (b) C(OCH$_3$)$_2$N(CH$_3$)$_2$, toluene, reflux, 2 hr.

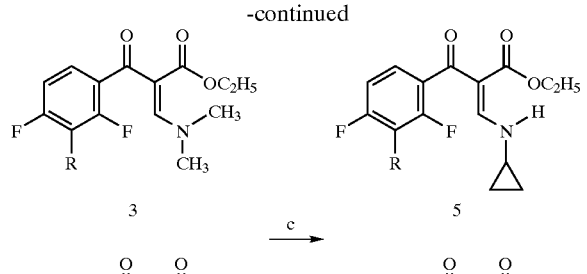

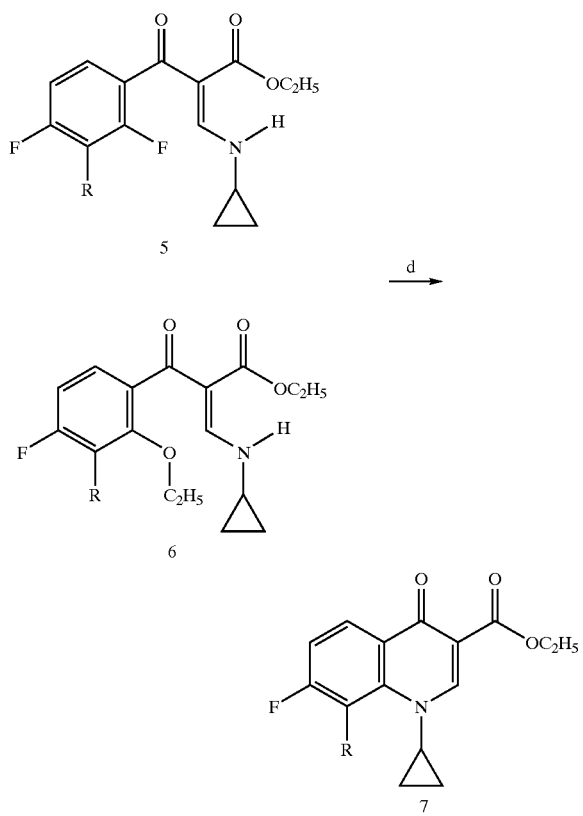

Reagents and conditions: (d) N,O-bis(trimethylsilyl)acetamide, toluene, reflux, 1 hr.

EXAMPLE 1

7-Fluoro-8-methoxyquinolone Ethyl Ester (7)

Preparation of 3-(2,4-difluoro-3-methoxyphenyl)-3-oxo-propionic acid ethyl ester and 3-(2-ethoxy-4-difluoro-3-methoxyphenyl)-3-oxo-propionic acid ethyl ester admixture (1 and 2): To a reaction vessel is charged toluene (2087 mL) and an oil dispersion of NaH containing 60% active base (264 g, 6.6 mol). Diethylcarbonate (850.5 g, 7.2 mol) is slowly added over 1 hour to the suspension of NaH at 90° C. 2,4-Difluoro-3-methoxyacetophenone (558 g, 3 mol) is dissolved in sufficient toluene to form a homogeneous solution (approx. 2 L) and this solution is added with care to the reaction vessel maintaining the reaction temperature within the range of 90° C.–95° C. Once the evolution of hydrogen gas has stopped, the reaction is stirred an additional 30 minutes after which the reaction is cooled to 20° C. and quenched with the addition of a 10% w/w aqueous solution of $H_2SO_4$ (3822 g). The layers are separated and the solvent is concentrated in vacuo (40° C. @<100 mbar), the toluene azeotrope utilized to dry the organic phase. The resulting admixture of compounds 1 and 2 is used without further purification.

Preparation of 2-(2,4-difluoro-3-methoxybenzoyl)-3-dimethylamino-acrylic acid ethyl ester and 2-(2-ethoxy-3-methoxy-4-fluorobenzoyl)-3-dimethylamino-acrylic acid ethyl ester admixture (3 and 4): To a reaction vessel is charged an admixture of 3-(2,4-difluoro-3-methoxyphenyl)-3-oxo-propionic acid ethyl ester and 3-(2-ethoxy-4-fluoro-3-methoxyphenyl)-3-oxo-propionic acid ethyl ester, 1 & 2, (850 g, ~3 mol) and toluene (3850 mL). Over a period of about 15 minutes dimethylformamide dimethyl acetal (536.3 g, 4.5 mol) is added after which the reaction is heated to about 90° C. and the methanol produced is allowed to distill off. The solution is then refluxed for about 2 hours. At this point the reaction sequence can be carried forward without isolation of 3 and 4. The products are isolated by concentrating the reaction solution in vacuo, taking up the residue in methylene chloride and extracting the resulting organic layer with water. Re-concentration in vacuo provides the admixture of 3 and 4.

Preparation of 3-cyclopropylamino-2-(2,4-difluoro-3-methoxybenzoyl)-acrylic acid ethyl ester and 3-cyclopropylamino-2-(2-ethoxy-3-methoxy-4-fluorobenzoyl)-acrylic acid ethyl ester admixture (5 and 6): The reaction from above, the admixture of 3 and 4, at the point after which the solution has been refluxed for about 2 hours, is cooled to room temperature and toluene is added (2087 mL). Cyclopropylamine (205.6 g, 3.6 mol) is added and stirring is continued at room temperature until the reaction is complete by TLC (about 30 minutes). The reaction is then quenched by adding a 10% aqueous solution of $H_2SO_4$ (2940 g, 3 mol). The organic layer is concentrated in vacuo until all presence of water is absent. The resulting toluene solution of 5 and 6 can be carried on to the ring closure reaction without further purification.

Preparation of 1-cyclopropyl-7-fluoro-8-methoxy-4-oxo-1,4-dihydro-quinoline-3-carboxylic acid ethyl este admixture of 3-cyclopropylamino-2-(2,4-difluoro-3-methoxybenzoyl)-acrylic acid ethyl ester and 3-cyclopropylamino-2-(2-ethoxy-3-methoxy-4-fluorobenzoyl)-acrylic acid ethyl ester, 5 and 6, (1050 g, ~3 mol) and toluene (4270 mL). N,O-Bis(trimethylsilyl)-acetamide (610.3 g, 3 mol) is added and the reaction is brought to reflux for 30 minutes. Additional N,O-bis(trimethylsilyl)-acetamide (183 g, 0.9 mol) is added to the reaction and heating is continued for an additional 30 minutes. The reaction is cooled and the solvent reduced in vacuo (40° C. @, 100 mbar). The solution is cooled in an ice bath and the solid which forms is collected by filtration, and wash twice with distilled water to afford 757 g (82% yield) of the desired product.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for preparing a quinolone antibiotic intermediate having the formula:

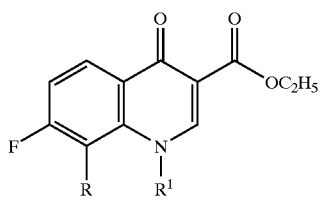

wherein R is $C_1$–$C_2$ alkyl, $C_1$–$C_2$ fluoroalkyl, $C_2$–$C_4$ alkenyl, methoxy, chloro, or bromo; $R^1$ is a unit selected from the group consisting of $C_1$–$C_2$ alkyl, $C_2$–$C_3$ alkenyl, $C_3$–$C_5$ cycloalkyl, and phenyl, each of which can be substituted by one or more fluorine atoms; said process comprising the step of cyclizing an admixture of quinolone precursors, said admixture comprising a 2-ethoxy substituted intermediate having the formula:

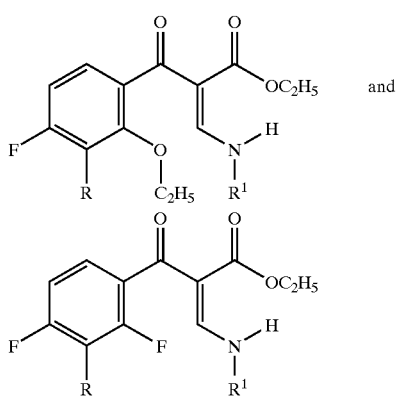 and in the presence of a silylating agent.

2. A process according to claim 1 wherein R is —$OCH_3$.
3. A process according to claim 1 wherein R is —$CH_3$, —$CH_2F$, —$CHF_2$, and —$CF_3$.
4. A process according to claim 1 wherein R is —Cl.
5. A process according to claim 1 wherein R is —$CH_2CH$=$CH_2$.
6. A process according to claim 1 wherein said cyclization is conducted in the presence of a solvent selected from the group consisting of methylene chloride, dichloromethane, hexamethylphosphoramide, tetrahydrofuran, benzene, toluene, alkanes, and mixtures thereof.
7. A process according to claim 1 wherein said silylating agent is selected from the group consisting of chlorotrimethylsilane, N,O-bis(trimethyl-silyl)acetamide, N,O-bis(trimethylsilyl)trifluoroacetamide, bis(trimethylsilyl)urea, hexamethyltrisilazane, N-methyl-N-trimethylsilyltrifluoroacetamide, 1-trimethylsilyl-imidazole, trimethylsilyl trifluourmethanesulfonate, tert-butyldimethylchlorosilane, 1-(ted-butyldimethylsilyl)imidazole, N-tert-butyldimethyl-N-methyltrifluoroacetamide, tert-butyldimethylsilyltrifluoromethanesulfonate, tert-butylphenylchorosilane, tert-butyl-methoxyphenylbromosilane, dimethylphenylchlorosilane, triethylchlorosilane, trimethylsilyl methoxyphenylbromosilane, dimethylphenylchlorosilane, triethylchlorosilane, trimethylsilyl trifluoromethanesulfonate, and triphenylchlorosilane.

8. A process according to claim 7 wherein said silylating agent is N,O-bis(trimethylsilyl)acetamide.

9. A process according to claim 1 wherein $R^1$ cyclopropyl, methyl, ethyl, and benzyl.

10. A process according to claim 1 wherein said cyclization is conducted by refluxing in the presence of a solvent.

11. A process for preparing a quinolone antibiotic intermediate having the formula:

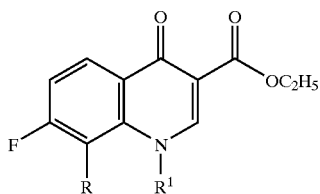

wherein R is $C_1$–$C_2$ alkyl, $C_1$–$C_2$ fluoroalkyl, $C_2C_4$ alkenyl, methoxy, chloro, or bromo; $R^1$ is a unit selected from the group consisting of $C_1$–$C_2$ alkyl, $C_2C_3$ alkenyl, $C_3$–$C_5$ cycloalkyl, and phenyl, each of which can be substituted by one or more fluorine atoms; said process comprising the steps of:

a) reacting an acetophenone having the formula:

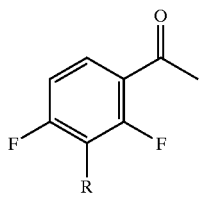

with diethylcarbonate in the presence of a base to form an admixture of 4-fluoro β-ketoesters having the formula:

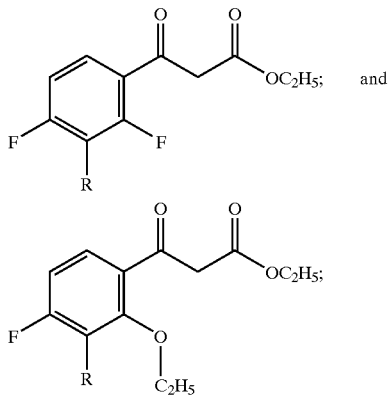

b) reacting said admixture with a compound capable of undergoing the Knoevenagel Reaction having the formula:

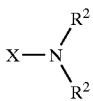

wherein $R^2$ is $C_1$–$C_4$ linear or branched alkyl, phenyl, and mixtures thereof; X is an aldehyde unit or an aldehyde unit equivalent; to form an admixture of imine intermediates having the formula:

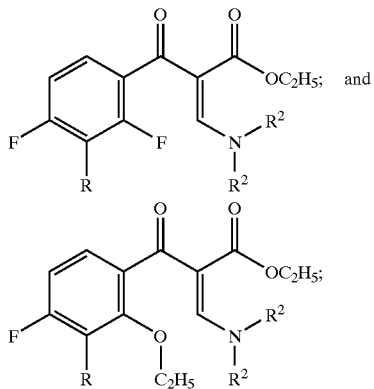

c) reacting said imine intermediate admixture with an amine having the formula:

to form an admixture of quinolone intermediates having the formula:

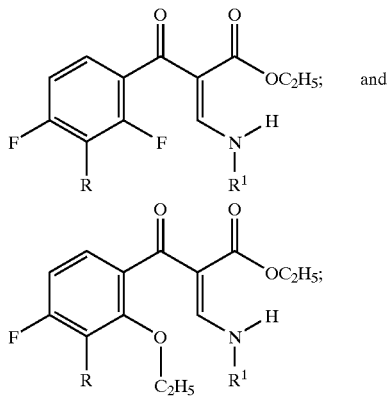

d) cyclizing said quinoline intermediate ate admixture in the presence of a silylating agents to farm said quinoline antibiotic intermediate having the formula:

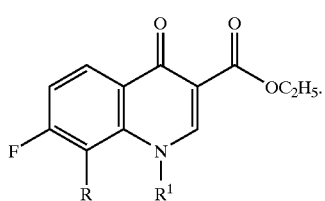

12. A process according to claim 11 wherein said base in step (a) is a metal hydride selected from the group LiH, NaH, KH, CaH₂ and mixtures thereof.

13. A process according to claim 11 wherein said base in step (a) is an inorganic base selected from the group Na₂CO₃, NaHCO₃, K₂CO and mixtures thereof.

14. A process according to claim 11 wherein said base in step (a) an organic base selected from butyl lithium and lithium diisopropylamide.

15. A process according to claim 11 wherein step (a) comprises reacting one mole of a substituted acetophenone with 2.2 moles of a base, and 2.4 moles of diethylcarbonate.

16. A process according to claim 11 wherein step (a) is conducted in the presence of a solvent selected from the group consisting of methylene chloride, dichloro-methane, hexamethylphosphoramide, tetrahydrofuran, benzene, toluene, alkanes, and mixtures thereof.

17. A process according to claim 11 wherein said adduct is an aldehyde having the formula:

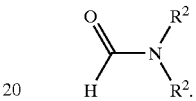

18. A process according to claim 11 wherein said adduct is a dimethyl acetal having the formula:

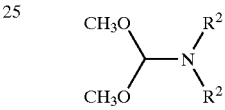

wherein $R^2$ is methyl, ethyl, and mixtures thereof.

19. A process according to claim 11 wherein step (b) is conducted in the presence of toluene wherein said adduct is a dimethyl acetal and wherein further the admixture obtained from step (a) and said dimethyl acetal is heated to azeotropically remove any methanol which is formed.

20. A process according to claim 11 wherein said primary amine in step (c) is selected from the group consisting of methylamine, ethylamine, and cyclopropylamine.

21. A process according to claim 11 wherein step (a) is conducted in the presence of a solvent selected from the group consisting of methylene chloride, dichloro-methane, hexamethylphosphoramide, tetrahydrofuran, benzene, toluene, alkanes, and mixtures thereof.

22. A process according to claim 11 wherein step (d) is conducted in the presence of a solvent selected from the group consisting of methylene chloride, dichloromethane, hexamethylphosphoramide, tetrahydrofuran, benzene, toluene, alkanes, and mixtures thereof.

23. A process according to claim 11 wherein said silylating agent is selected from the group consisting of chlorotrimethylsilane, N,O-bis(trimethyl-silyl)acetamide, N,O-bis(trimethylsilyl)trifluoroacetamide, bis (trimethylsilyl)urea, hexamethyltrisilazane, N-methyl-N-trimethylsilyltrifluoroacetamide, 1-trimethylsilyl-imidazole, trimethylsilyl trifluourmethanesulfonate, tert-butyldimethylchlorosilane, 1-(tert-butyldimethylsilyl) imidazole, N-tert-butyldimethyl-N-methyltrifluoroacetamide, tert-butyldimethylsilyl-trifluoromethane sulfonate, tert-butylphenylchorosilane, tert-butyl-methoxyphenylbromosilane, dimethylphenylchlorosilane, triethylchlorosilane, trimethylsilyl trifluoromethanesulfonate, and triphenylchlorosilane.

24. A process according to claim 23 wherein said silylating agents is N,O-bis(trimethylsilyl)acetamide.

25. A process according to claim 11 wherein atop (d) is conducted by reflecting in the presence of a solvent.

* * * * *